(12) United States Patent
Klemm (10) Patent No.: US 7,624,737 B2
(45) Date of Patent: Dec. 1, 2009

(54) ANTERIOR SUPPORT DEVICE

(75) Inventor: Kurt W. Klemm, Rhinelander, WI (US)

(73) Assignee: Pilgrim Innovations, LLC, Omro, WI (US)

(*) Notice: Subject to any disclaimer, the term of this patent is extended or adjusted under 35 U.S.C. 154(b) by 550 days.

(21) Appl. No.: 10/833,652

(22) Filed: Apr. 28, 2004

(65) Prior Publication Data

US 2004/0226567 A1 Nov. 18, 2004

Related U.S. Application Data

(60) Continuation-in-part of application No. 10/427,108, filed on Apr. 30, 2003, now Pat. No. 7,422,016, which is a continuation-in-part of application No. 10/180,621, filed on Jun. 26, 2002, which is a division of application No. 09/932,041, filed on Aug. 17, 2001, now Pat. No. 6,435,186.

(51) Int. Cl.
*A61F 5/56* (2006.01)
*A47B 7/00* (2006.01)
*B68G 5/00* (2006.01)

(52) U.S. Cl. .................. 128/848; 128/845; 128/846; 5/623; 5/624; 5/646; 248/118

(58) Field of Classification Search ............... 128/845, 128/846; 5/623, 624, 646, 648, 507.1; 248/118, 248/118.1, 121, 122.1, 424; 297/105–114, 297/170–172, 217.7, 227, 219.1, 256.1, 256.11, 297/256.13, 258.1, 344.1; 119/753–757
See application file for complete search history.

(56) References Cited

U.S. PATENT DOCUMENTS 135,435 A 2/1873 Lyons (Continued)

FOREIGN PATENT DOCUMENTS

WO 03017859 3/2003

(Continued)

OTHER PUBLICATIONS

Kobo Chair, internet, http://www.kobochair.com/iframes/productinfo.html, 1 page, date printed Oct. 13, 2005.

(Continued)

*Primary Examiner*—Michael Phillips
*Assistant Examiner*—Tarla R Patel
(74) *Attorney, Agent, or Firm*—Thomas J. Connelly; Thomas D. Wilhelm; Wilhelm Law, S.C.

(57) ABSTRACT

A support device and associated appurtenances, which support a user's torso while in a forward leaning position. The device includes a rest the user can lean his/her torso on while working in a forward leaning position, and support structure adapted which can adjust the angle, height, and/or lateral position of the rest. A support device includes support structure, and a rest supported by the support structure, from a base. The rest can support the torso of a user, from the base, as the user leans his/her torso against the rest. Transport structure can be used to move the support structure back and forth along the base. One or more pivotations can be used from base to rest. The invention is useful anywhere a user leans forward for an extended time, such as dentists, working over a desk, over a drafting table, or over a manufacturing line or assembly line.

39 Claims, 10 Drawing Sheets

U.S. PATENT DOCUMENTS

| | | | |
|---|---|---|---|
| 2,038,806 A | 4/1936 | Sellar | |
| 2,519,771 A | 8/1950 | Lacore | |
| 3,216,767 A | 11/1965 | Lutfy | |
| 3,848,838 A | 11/1974 | Thomas | |
| 3,897,778 A | 8/1975 | Forbes-Robinson et al. | |
| 3,977,645 A | 8/1976 | Deely | |
| 4,397,374 A * | 8/1983 | Rumage et al. | 182/129 |
| 4,727,958 A * | 3/1988 | Botello | 182/15 |
| 4,917,343 A | 4/1990 | Wainscott | |
| 5,118,062 A | 6/1992 | Archambault | |
| 5,281,001 A | 1/1994 | Bergsten et al. | |
| 5,295,728 A | 3/1994 | Schaevitz | |
| 5,545,177 A | 8/1996 | Coseo | |
| 5,887,948 A * | 3/1999 | Hannes | 297/411.35 |
| 6,102,344 A * | 8/2000 | Kasvin et al. | 248/118 |
| 6,138,970 A | 10/2000 | Sohrt et al. | |
| 6,309,329 B2 | 10/2001 | Conner | |
| 6,435,186 B1 | 8/2002 | Klemm | |
| 6,553,918 B2 | 4/2003 | Bieza | |
| 6,554,238 B1 | 4/2003 | Hibberd | |
| 6,629,944 B2 | 10/2003 | Smart | |
| 6,644,748 B2 * | 11/2003 | Tholkes et al. | 297/423.12 |
| 6,708,935 B2 | 3/2004 | Smeed | |
| 2002/0158492 A1 | 10/2002 | Ko et al. | |
| 2005/0015879 A1 | 1/2005 | Cuschieri et al. | |

FOREIGN PATENT DOCUMENTS

WO    2005023072    3/2005

OTHER PUBLICATIONS

AliMed, Medical & Ergonomic Products . . . Internet, www.alimed.com/ ProductDetail.asp?style=73251; date printed Dec. 4, 2006.

Dentech Advance Stools, internet, http://www.dentechcorp.com/products/ stools.html; p. 1-2, date printed Mar. 27, 2007.

Office Organix, Advanced Ergonomics @ Internet Prices, internet, www.officeoganix.com/NPAbstool.htm; pp. 1-5, date printed Mar. 19, 2007.

Kobo Chair by DK&E Technology, internet, http://www.kobochair.com/products.html Date printed Mar. 19, 2007.

* cited by examiner

ANTERIOR SUPPORT DEVICE

PRIORITY CLAIM

This application claims priority under 35 U.S.C. 120 from application Ser. No. 10/427,108 filed Apr. 30, 2003, which claims priority under 35 U.S.C. 120 from application Ser. No. 10/180,621 filed Jun. 26, 2002, which claims priority under 35 U.S.C. 120 from application Ser. No. 09/932,041, now U.S. Pat. No. 6,435,186, issued Aug. 20, 2002, both of which are incorporated herein by reference in their entireties.

BACKGROUND

The present invention is directed generally to a support device and specifically to an anterior support device for use in the health care industry and other environments where a person leans forward, leans forward repeatedly, and/or leans forward for extended periods of time. The invention relates to use of an anterior support devise in a variety of body postures, including, without limitation, generally upright, e.g. standing posture, kneeling posture, sitting posture and any other postures where the center of mass of the body, e.g. the trunk, projects forwardly of the underlying base from which the body is supported. The invention further relates to use of a support device to provide a support base to support a person who is in an upright orientation and otherwise balanced with no current lean.

Many individuals suffer from lower back pain and dysfunction brought about by their work environment or other daily activities. Repetitive or prolonged activities can be attributed as a major cause of this back pain and dysfunction. Affected individuals must drastically modify their work areas in order to continue their jobs. In many instances, people must choose another field of employment.

One such example is dentists. Dentists spend a good deal of their workday leaning over patients, in a forward bent position. This position contributes to posterior disc dysfunction and/or other factors which can lead to back pain and disability. For dentists, back pain is one of the leading causes of early retirement.

To alleviate such back pain, some individuals turn to physical therapy. Others attempt to support their backs while on the job by using braces and cushions that are intended to support the spine in a normal, anatomical erect position. These devices, however, are designed to support the individual from the rear and thus are not effective for dentists and other individuals who must be in a forward bent position, or forward leaning position, as a fundamental part of their work, or other activity.

Thus, there is a need in the art for a device which supports an individual's spine while the individual is in a forward bent position, or forward leaning position.

There is a further need in the art for a device which decreases the stress on the lower, middle, and upper back experienced by individuals while in a forward bent position or forward leaning position.

There is yet a further need in the art for a device which extends the productive life of individuals who perform repetitive or prolonged forward leaning activities, or forward bending activities as part of their employment or daily activities.

SUMMARY

This invention comprises an anterior support device which includes support structure, and a rest supported by the support structure, from a base. The rest is adapted and configured to support the torso of a user, from the base, as the user leans the front side of his/her torso against the rest. The support device can include transport structure as interface between the support structure and the base, thus to enable the support structure to be moved back and forth along the base, transverse to the longitudinal direction of lean of the torso of the user against the rest, thereby to move the rest to the left and/or right along the base, with respect to the user. The support device, as an assembly, can include one or more pivot structures, e.g. between the base and the support structure, between the base and the transport structure, within the support structure, between the support structure and the rest, or within the rest. Such pivot structure typically pivots about an axis of pivotation which extends transverse to the longitudinal direction of lean of the torso of the user against the rest, thereby to adjust the angle of the top surface of the rest, with respect to a horizontal plane, at which the rest receives the torso of the user. Support devices of the invention are useful anywhere a user leans or bends forward for an extended period of time, such as over a patient in a dental chair, over a desk, over a drafting or drawing table, over an auto engine compartment, over a manufacturing line or assembly line, or other work area in a manufacturing or other environment.

In a first family of embodiments, the invention contemplates a support device adapted and configured to support a torso of a user from a base. The support device can comprise transport structure adapted and configured to be coupled to the base; support structure operatively coupled to the transport structure and extending away from the transport structure; and a rest, against which the user can lean so as to support the torso of the user. The rest is operatively coupled to the support structure. The support structure and the transport structure are cooperatively adapted and configured such that (i) the support structure can be moved along the transport structure and along the base, and such that (ii) the support structure can be temporarily fixed in position relative to the base, against all movement with respect to the base, and subsequently released from the fixation so as to again enable movement of the support structure along the transport structure.

In some embodiments, the transport structure is adapted and configured to be operatively coupled to one of the group consisting of a dental chair, a base adjacent a dental chair, a desk, a base adjacent or on a manufacturing line, or other work station.

In some embodiments, the invention comprises a support assembly which comprises a such support device, which further comprises a base to which the transport is operatively coupled, the base optionally comprising a work station in a manufacturing facility.

In some embodiments, the support device further comprises pivot structure operatively engaged in and/or with at least one of the rest, the support structure, and the transport structure, and optionally enabling the rest to pivot with respect to the support structure.

In some embodiments, the pivot structure further comprises extension structure operative with at least one of the transport structure, the support structure, and the rest, so as to enable the rest to be extended further away from, and/or retracted toward, the base.

In some embodiments, the transport structure comprises a track, having a length, the support structure being operatively movable along the length of the track, and wherein optionally at least one of the track and the support structure comprises locking structure adapted and configured to temporarily lock the support structure against movement along the length of the track.

In a second family of embodiments, the invention comprehends a support device adapted and configured to support a forward-leaning torso of a user from a base. The support device comprises transport structure adapted and configured to be movably coupled to the base so as to be enabled to move in a direction along a linear path; support structure operatively coupled to the transport structure and extending away from the transport structure; and a rest, having a front and a rear. An imaginary line between the front and the rear of the rest extends transverse to the linear path of movement of the transport structure. The rest is adapted and configured, and so mounted to the support structure, that a user can approach the rest from the front, and lean the user's torso forward on the rest, and transverse to the linear path, in a front-to-rear direction thereby to support the torso of the user.

In some embodiments, the rest pivots with respect to the support structure, about a pivot axis which extends in a direction parallel to at least a portion of the linear path traversed by the transport structure.

In a third family of embodiments, the invention comprehends a support device adapted and configured to support a torso of a user from a base. The support device comprises transport structure adapted and configured to be coupled to the base; support structure operatively coupled to the transport structure and extending away from the transport structure; and a rest, against which the user can lean, so as to support the torso of the user, the rest being pivotably coupled to the support structure by pivot structure, so as to pivot with respect to the support structure.

In some embodiments, the rest has a front and a rear, and the rest is adapted and configured such that the user can approach the rest from the front, and lean the user's torso forwardly onto the rest, and across an axis of pivotation of the pivot structure.

In a fourth family of embodiments, the invention comprehends a vocational work station adapted and configured for production of work by a worker. The vocational work station comprises a substrate effective to support an object on which work is to be performed; and a support assembly, generally fixedly positioned relative to the substrate, the support assembly comprising (i) a base, (ii) support structure operatively coupled to the base and extending away from the base, and (iii) a rest, against which a user can lean so as to support the torso of such user while working on such object in association with the substrate, the rest being operationally associated with the support structure.

In some embodiments, the vocational work station further comprises transport structure, coupled to the base, and serving as an interface between the base and the support structure, so as to enable movement of the rest with respect to the base and the substrate.

In some embodiments, the vocational work station further comprises pivot structure operatively engaged in and/or with at least one of the rest and the support structure.

In a fifth family of embodiments, the invention comprehends a manufacturing facility, comprising at least first and second work stations where manufacturing work is to be performed by workers as the predominant work at the work stations. The at least first and second work stations comprise support assemblies. A such support assembly comprises a base; support structure operatively coupled to the base and extending away from the base; and a rest, against which a worker can lean so as to support the torso of the worker, the rest being operatively coupled to the support structure.

In some embodiments, the support assembly further comprises transport structure, coupled to the base, and serving as an interface between the base and the support structure, the coupling of the transport structure to the base being operative to enable movement of the transport structure, and thus the support assemblies, with respect to the base.

In some embodiments, the at least first and second work stations are disposed inside a generally closed building.

In some embodiments, the rest comprises an interfacing top surface sufficiently expansive in length and width that a user thereof can comfortably lean the user's weight on the interfacing top surface, at the torso of the user, and wherein the support assembly includes adjustment structure which enables adjustment of the rest with respect to the base, regarding at least one of height of the rest, and angle of the interfacing top surface, with respect to a horizontal plane.

In some embodiments, the adjustment structure enables the rest to pivot with respect to the support structure.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
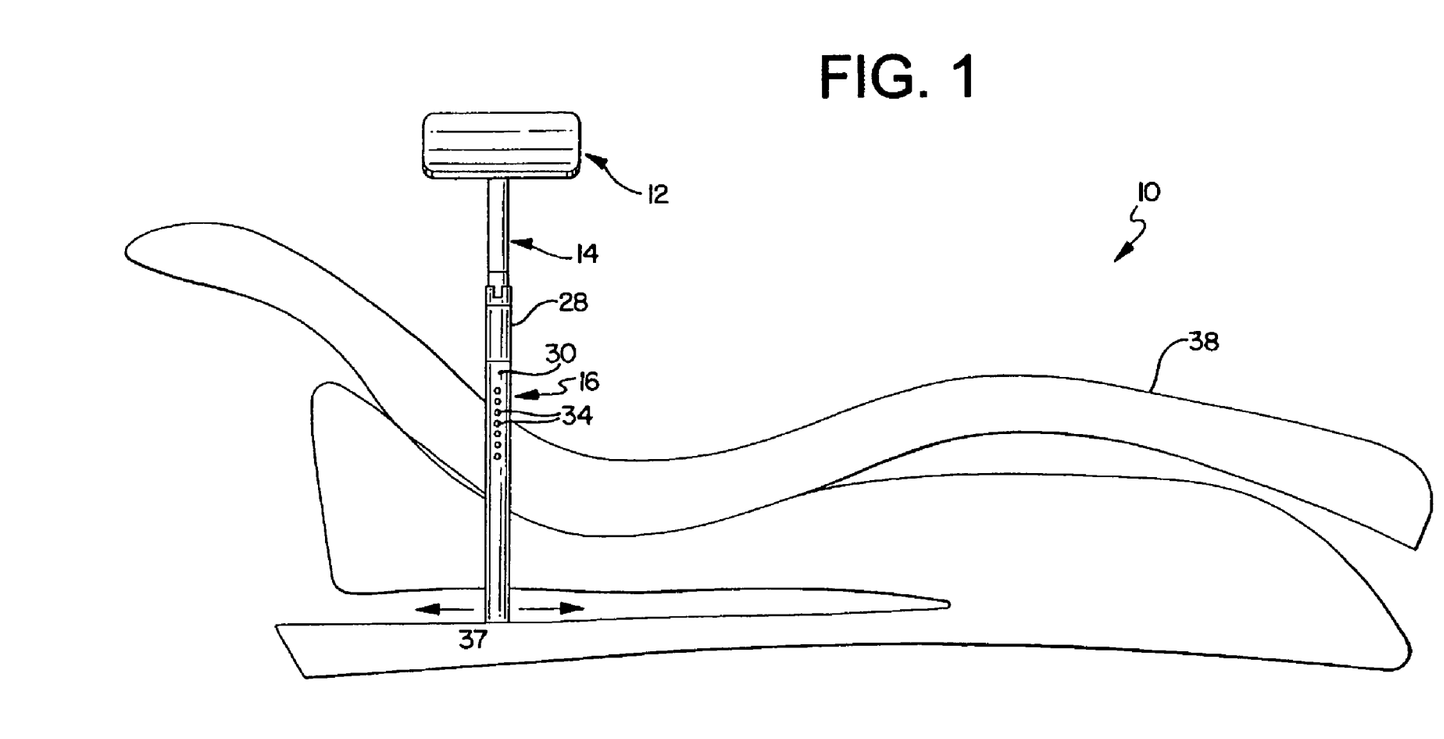
FIG. 1 is a perspective view of the invention mounted adjacent a dental chair.
Figure 2:
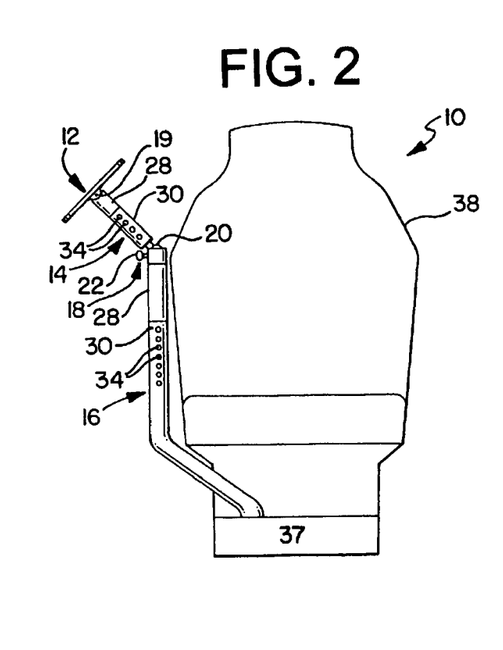
FIG. 2 is a front view of the device shown in FIG. 1.

In the embodiments illustrated in FIGS. 1 and 2, the support device 10 of the present invention generally includes a padded rest 12, an angled bracket 14, and an upright bracket 16. The padded rest 12 can pivot with respect to the angled bracket 14. This pivoting is enabled due to the presence of a single or multi-axial pivot device 19, illustrated in FIG. 2.

Referring to FIG. 2, bracket 14 extends at an angle from the upright bracket 16 so that the rest 12 is positioned to support the practitioner near the patient. To accomplish this, a coupler 18 is provided between angled bracket 14 and upright bracket 16 to allow rest 12 to be tilted in any direction. Once the angular position of bracket 14 with respect to upright bracket 16 is adjusted to the desired position, coupler 18 can be used to lock the angled bracket in that desired position, angular orientation.

Figure 6:
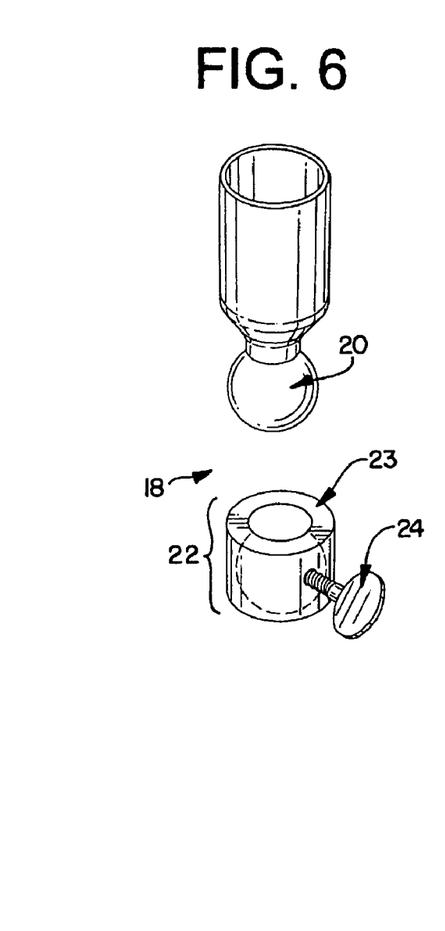
FIG. 6 is a partially exploded, perspective view of a coupler useful in the invention.

Preferably, coupler 18 comprises a ball swivel 20 having a screw friction lock 22, as shown in FIG. 6. The friction lock 22 comprises a retainer 23 into which the ball end of the bracket is inserted and a screw tightener 24 for locking the bracket in the desired position, orientation. Other locking devices are contemplated in place of, or in combination with, screw friction lock 22.

Figure 7A:
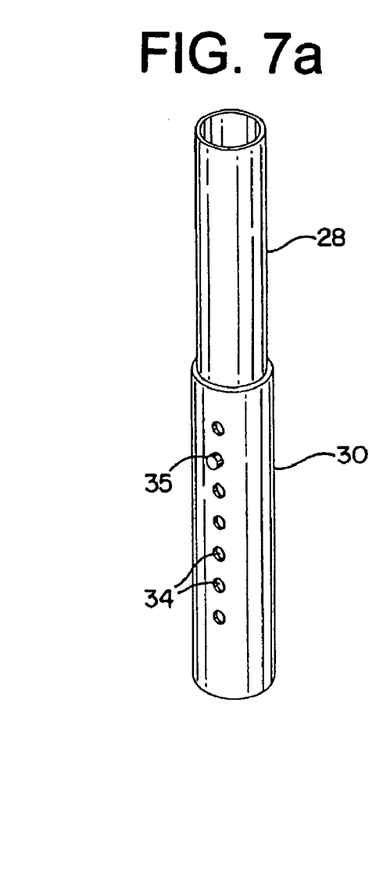
FIGS. 7a and 7b are exemplary perspective views of the telescoping feature of the invention.

Brackets 14 and 16 can be adjustable in length so that the distance of rest 12 from the patient can be varied as needed. Although the figures depict both brackets as being adjustable in length, the invention does contemplate embodiments wherein only one of brackets 14, 16 is adjustable. To enable this adjustability, at least one of the brackets 14, 16 comprises a first bracket member 28 carrying a spring-loaded pin lock 35 and a second bracket member 30 which has a plurality of adjusting holes 34. Details of the adjustment structure can be seen in FIGS. 7a and 7b. First member 28 is received into, and telescopes with respect to, second member 30 in a conventional manner of telescoping tubular elements, wherein pin lock 35 is advanced along the length of second member 30 in such orientation of the first and second members 28, 30 that pin 35 does not come into alignment with any of holes 34. This telescoping allows the overall length of the respective bracket to be adjusted. Once the desired length of the bracket is obtained, the first and/or second members 28, 30 are re-oriented, again in a conventional manner such as by relative rotation, to bring pin 35 into alignment with one of holes 34, whereupon pin 35 springs into the respective hole 34 of the second bracket member 30, as shown in FIG. 7a. The pin 35 functions to lock bracket member 28 at the desired length with respect to bracket member 30. Thus, the overall length of the device can be varied by adjusting the length of one or both of brackets 14, 16.

Figure 7B:
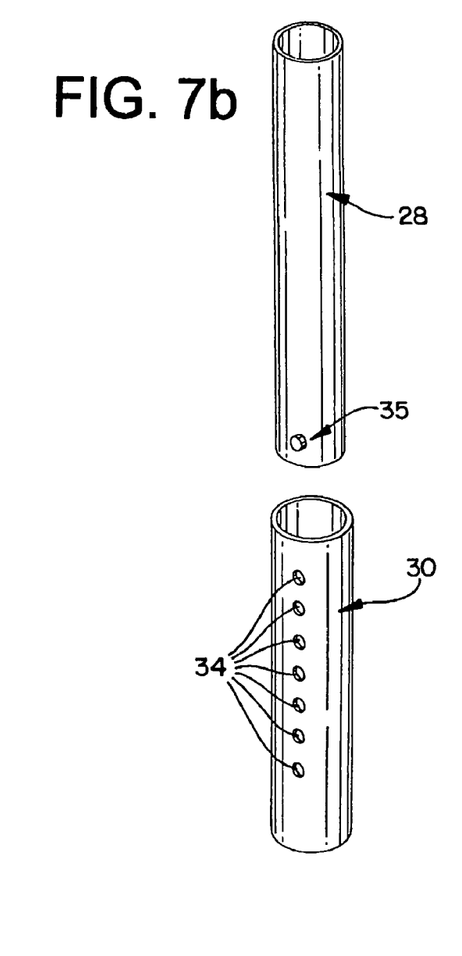

Although not shown in FIGS. 7a and 7b, member 28 can be provided with two spring loaded pin locks 35, one on each side of the member. Similarly, member 30 can be provided with two arrays of adjusting holes 34, the arrays being 180 degrees apart around the perimeter of member 30. In such case, member 28 is held at the desired length by the interaction of both pin locks 35 with their respective arrays of adjusting holes 34. Such use of two complementary pin locks facilitates the bracket remaining at the desired length.

Figure 8:
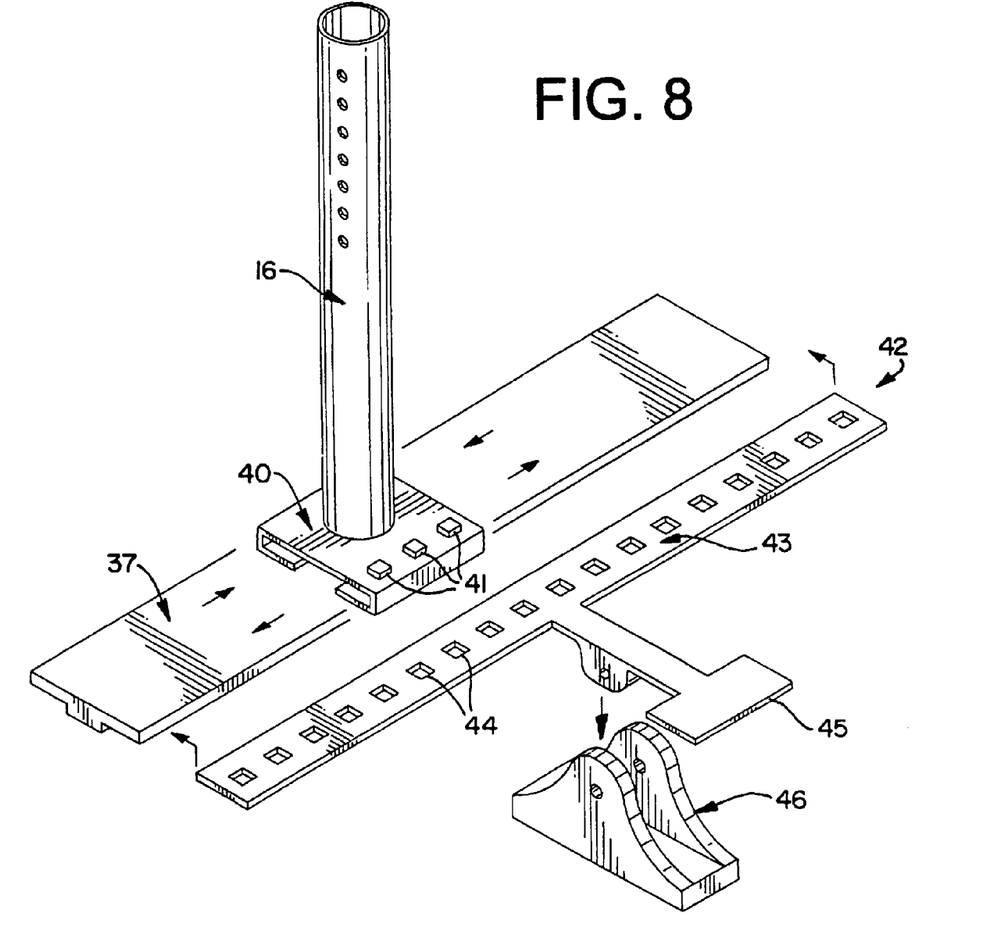
FIG. 8 is a partially exploded, perspective view of coupling and locking mechanisms of the invention for use with a dental chair.

As can be seen in FIGS. 1 and 2, the lower end of bracket 16 is mounted to a track 37 which is positioned adjacent the base of the dental chair 38. Referring to FIG. 8, the lower end of the bracket 16 is provided with a slide plate 40 for coupling or riding along track 37, the slide plate including raised locking pins 41. The coupling and corresponding sliding of bracket 16 along the length of track 37 enables the support device, namely rest 12, to be moved along the base of chair 38.

To lock bracket 16 in the desired position along track 37, a foot-controlled lock 42 is provided. Lock 42 comprises a spring-loaded locking bar 43 and a pivoting mount 46. The locking bar 43 includes a series of locking holes 44 and a footplate 45 extending from the bar. When bracket 16 is in the locked position on track 37, locking bar 43 is positioned above slide plate 40, with ones of the locking holes 44 engaging respective raised locking pins 41 of the slide plate 40. To release bracket 16 from the locked position, the user steps down on footplate 45, thereby causing locking bar 43 to pivot about pivoting mount 46. This pivoting results in locking holes 44 disengaging from locking pins 41. Bracket 16 can then be moved to a new position along track 37 where respective ones of holes 44 are positioned above pins 41, and in alignment with pins 41. To lock bracket 16 in the new position, the professional merely releases footplate 45. Footplate 45 is biased into contact with slide plate 41, and holes 44 again engage the underlying pins 41. Thus, the position of device 10 can be changed laterally, to the left or right as shown by the arrows in FIG. 8, to accommodate the preference of the professional or the particular patient.

Padded rest 12 can be used by a professional worker such as a dentist or a dental hygienist to lean over a patient while working on the patient. Since the back of the worker is supported from the front, or anterior side, of the torso, while in this bent, leaning, position, the stress experienced by the worker in his or her lower, middle, and/or upper back is reduced, compared to the same position without such support. Because the source of the support is anterior, the worker can assume any degree of forward lean to accomplish the required task and still be supported.

In accord with the adjustability of the angle of bracket 14 with respect to bracket 16, padded rest 12 can be tilted in any of a wide variety of directions and orientations to accommodate a particular body type or gender. The amount of padding is variable to allow the worker to change the contact points of the rest. Depending upon the comfort and preference of the worker, the rest can contact the worker in the abdominal area, in the chest area, or in the anterior shoulder area.

To use the present invention, the worker adjusts the angle of the bracket 14, the height of bracket 14 and/or bracket 16, and the position of bracket 16 with respect to dental chair 38. Then the worker can lean forward against rest 12, while working on the patient. Alternately, the worker can sit in a chair and lean against rest 12 to work on the patient. Because the worker is enabled to lean against rest 12, the back stresses experienced by the worker, while in such forward leaning position, are reduced.

Figure 9:
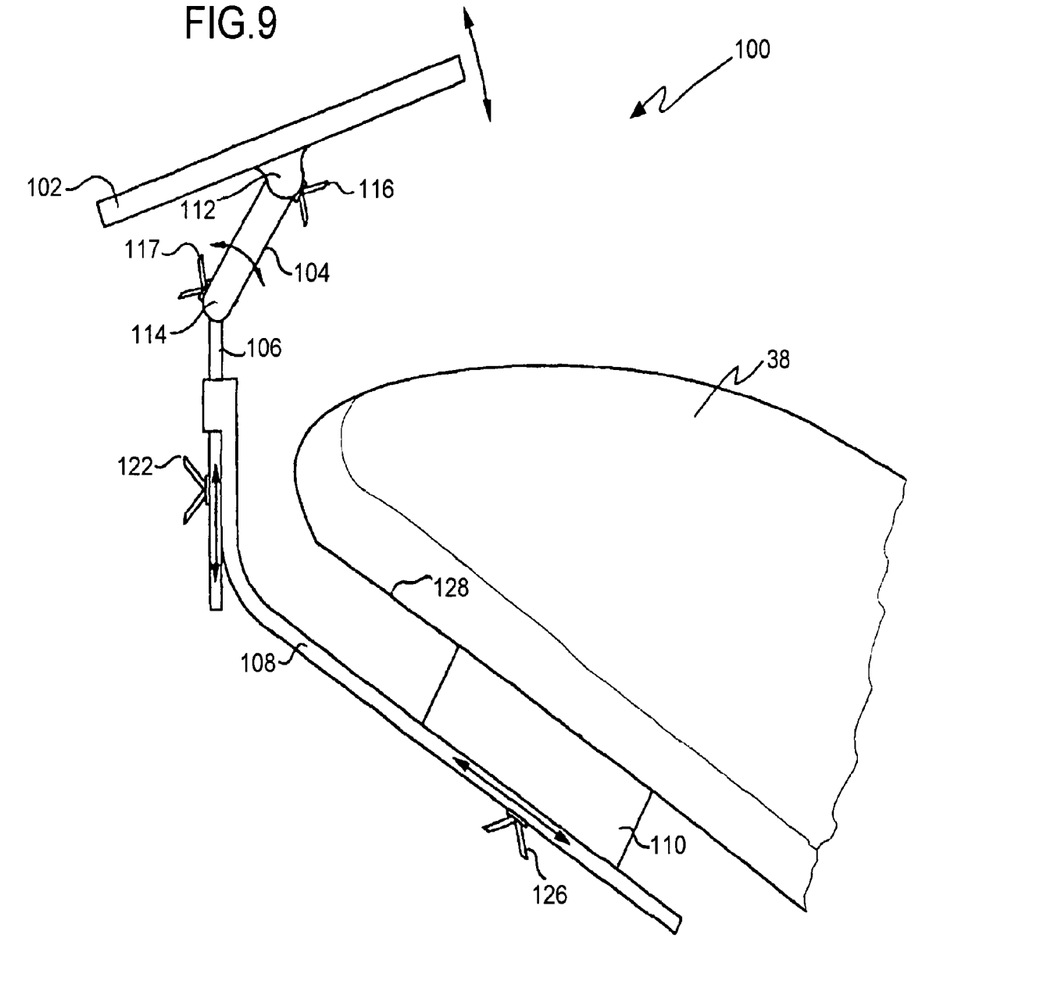
FIG. 9 is a side view of an alternative embodiment of the invention in use on a dental chair.
Figure 10:
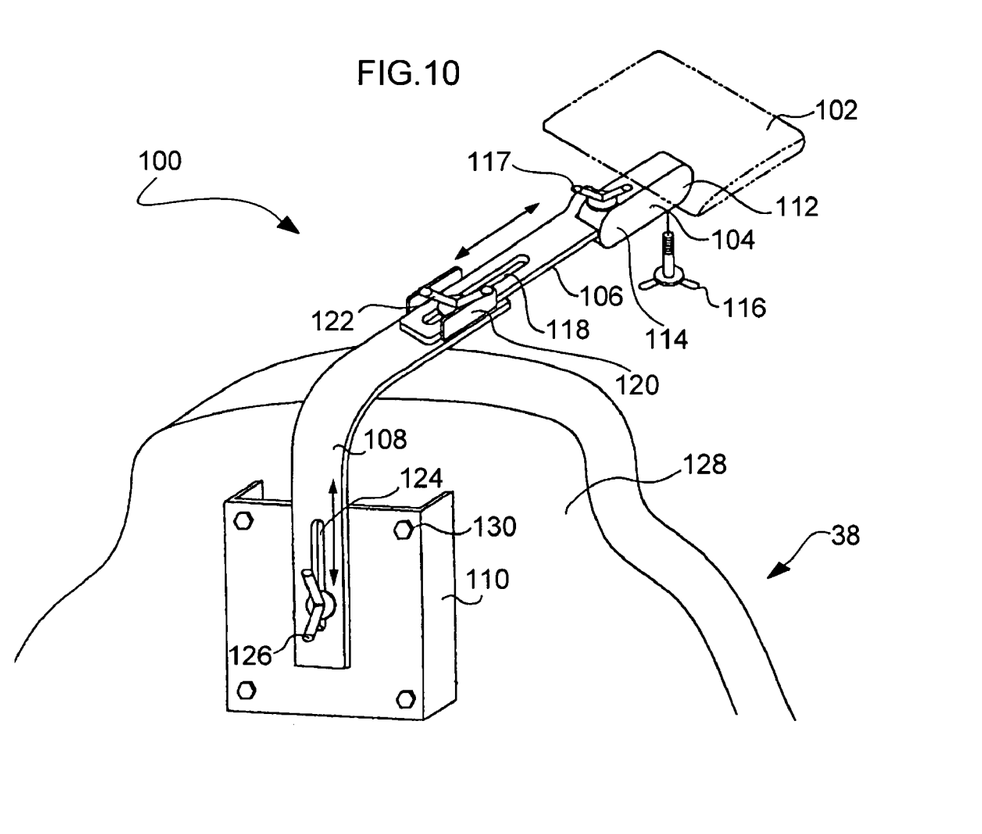
FIG. 10 is a perspective view of the device shown in FIG. 9.
Figure 11:
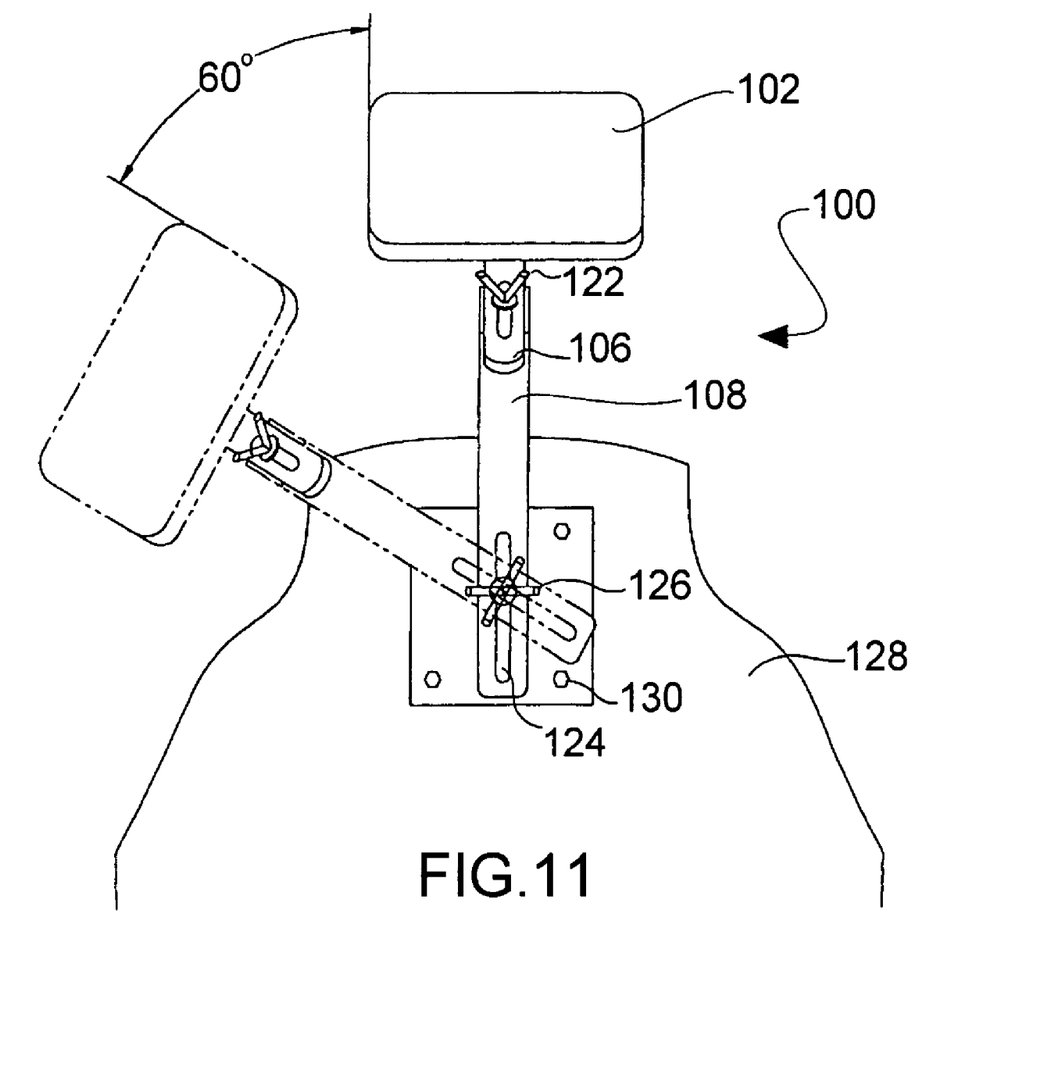
FIG. 11 is a rear view of the device shown in FIG. 9.

An alternate embodiment 100 of the present invention for use with a dental chair is shown in FIGS. 9-11. The alternate embodiment device 100 is similar to device 10 of FIG. 1, but differs in its relationship to dental chair 38. Instead of being attached to the base of dental chair 38, or to the floor, the device 100 is attached to the back of the dental chair. As can be seen in FIG. 11, the device 100 can be rotated from one side of the dental chair 38 to the other, thereby providing flexibility by enabling the worker to work on either side of the patient. The device also allows the angle, height, and position of the rest to be adjusted, thereby providing further flexibility. Alternatively, a support device of the invention can be attached to other locations on dental chair 38, such as at a side of dental chair 38.

As depicted in FIGS. 9-11, support device 100 of this embodiment generally includes a padded rest 102, a pivot device 104, a first or upper arm 106, a second or lower arm 108, and a mounting plate 110. In this embodiment, support device 100 can be added to dental chair 38 as an after-market item. An alternative embodiment is provided in FIG. 12, and is further described below, in which device 100 can be provided on dental chair 38 during manufacture of the chair.

Returning to FIGS. 9-11, padded rest 102 can be substantially the same as padded rest 12 depicted in FIG. 1. Accordingly, padded rest 102 can be formed in various shapes and sizes to accommodate a particular body type and/or gender. Padded rest 102 is attached to pivot device 104 through a pivot point 112 proximate a first end of pivot device 104. Similarly, the first end of upper arm 106 is attached to pivot device 104 through a second pivot point 114 proximate a second end of pivot device 104. Pivot device 104 enables the angular position of padded rest 102 to be adjusted by pivotation about pivot points 112, 114. Once padded rest 102 has been adjusted to the desired angular position, the position of padded rest 102 can be locked into place with a fastener 116 located at first pivot point 112 and a fastener 117 located at second pivot point 114. Fasteners 116, 117 are depicted in FIG. 9 as mating screws; however, fasteners 116, 117 can be any type of screw or other coupling device. Additionally, fastener 116 can be the same or a different type of fastener as fastener 117. Other methods of attaching padded rest 102 to upper arm 106 are also possible and are contemplated as being within the scope of the invention.

The height of device 100 can be adjusted. Providing a fastener and slot arrangement on both upper and lower arms 106, 108 enables such adjustment feature. As can be seen in FIG. 10, a second end of upper arm 106 is provided with a first slot 118. The second end of upper arm 106 is guided along rails 120 provided on a first end of lower arm 108. Once the desired height is obtained, a fastener 122 is inserted into first slot 118 and into a hole provided on the first end of lower arm 108, thereby securing upper arm 106 at the desired height with respect to lower arm 108. Fastener 122 is depicted in FIGS. 9-11, and 13 as a mating screw; however, fastener 122 can be any type of screw or other coupling device. Other methods of attaching upper and lower arms 106, 108 to each other are possible and are contemplated as being within the scope of the invention.

The slot and screw arrangement, which is provided on the second end of lower arm 108, enables support device 100 to be rotated, from one side of dental chair 38 to the other. In a preferred embodiment, device 100 can rotate 120 degrees from one side of dental chair 38 to the other. However, device 100 is not limited to that range of motion.

As can be appreciated from FIG. 11, to adjust the angular position of device 100, fastener 126 is loosened, the angular position of device 100 is adjusted (as shown in the dotted lines), and fastener 126 is again tightened. Thus, this arrangement allows device 100 to be locked at each position, thereby providing flexibility by enabling the professional to work on either side of the patient. At the same time the angular position of device 100 is adjusted, the height of device 100 can also be adjusted by sliding lower arm 108 along slot 124 and tightening fastener 126 once the desired height is obtained.

Device 100 can be mounted to dental chair 38 via a mounting plate 110. FIGS. 9-11 show mounting plate 110 attached to back 128 of the dental chair; however other mounting locations are possible, such as a side of dental chair 38. While mounting plate 110 is depicted in FIGS. 10-11 as being positioned substantially in the center of back 128 relative to the sides of dental chair 38, mounting plate 110 can be positioned anywhere on back 128 of the chair.

Mounting plate 110 can be fastened to back 128 of dental chair 38 with a plurality of fasteners 130, such as screws. FIG. 10 depicts mounting plate 110 being fastened to back 128 of dental chair 38 with four screws; however, the number and type of fasteners can vary in accord with known technology.

Figure 12:
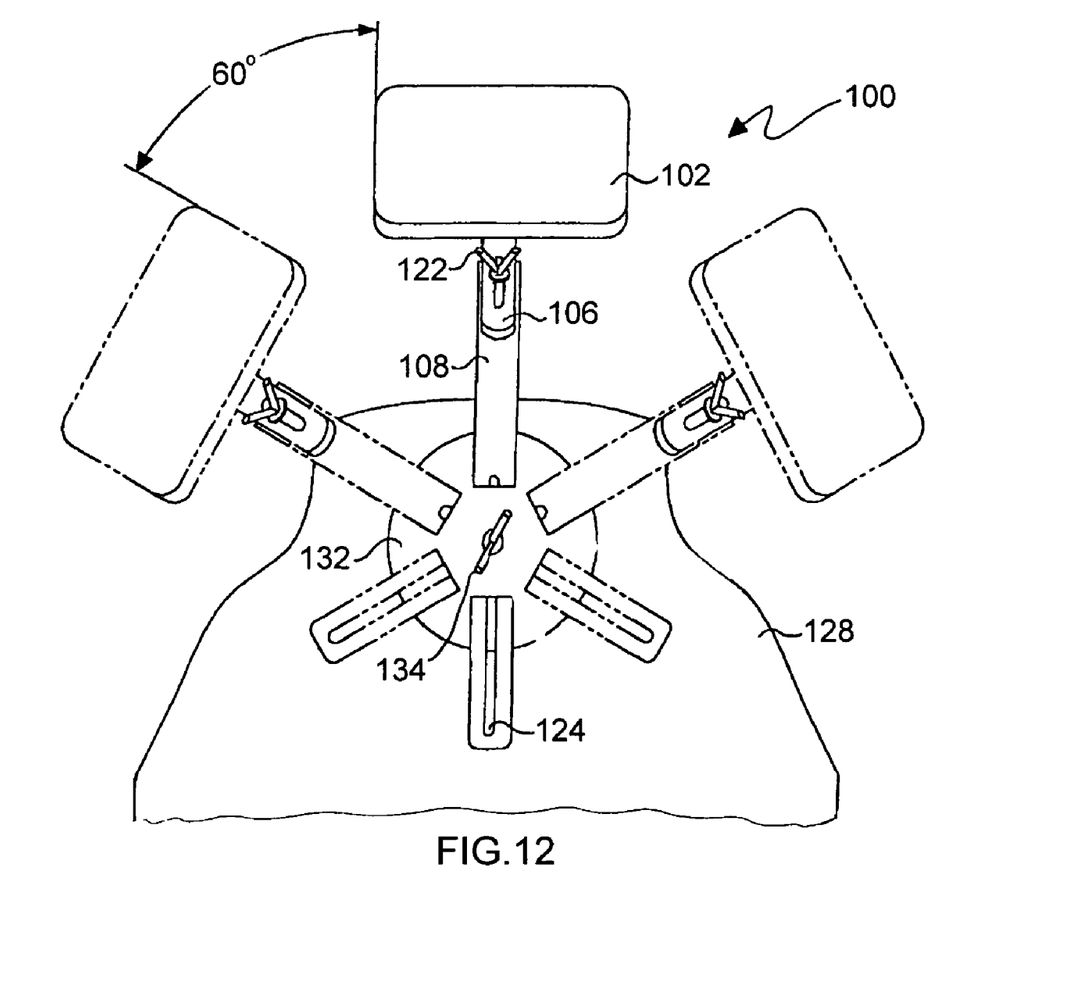
FIG. 12 is a rear view of an alternative embodiment of the invention in use on a dental chair.

FIG. 12 provides an alternative third embodiment for mounting device 100 to dental chair 38. In this embodiment, device 100 can be provided on dental chair 38 during original equipment manufacture of the chair as well as being available as an after-market product. Accordingly, instead of using a mounting bracket 110, device 100 is attached to back 128 of dental chair 38 using a rotatable base 132. Rotatable base 132 can be integral with dental chair 38 or can be a separate device added to dental chair 38 during manufacture.

While rotatable base 132 is depicted in FIG. 12 as being positioned substantially in the center of back 128 relative to the sides of dental chair 38, rotatable base 132 can be positioned anywhere on back 128. Additionally, rotatable base 132 can be attached to other locations on dental chair 38, such as at a side of the dental chair.

Rotatable base 132 comprises rotation structure which enables device 100 to be rotated (as shown in dotted lines), from one side of dental chair 38 to the other. In a preferred embodiment, device 100 can rotate 120 degrees from one side of the dental chair 38 to the other. However, device 100 is not limited to that range of motion.

At the same time that the angular position of support device 100 is adjusted, the height of device 10 can also be adjusted, by sliding lower arm 108 along slot 124. In this embodiment, a fastener 134 enables device 100 to be locked at each position, thereby providing flexibility by enabling the professional to work on either side of the patient, or from behind the patient. The fastener 134 is depicted in FIG. 12 as a mating screw; however, fastener 134 can be any type of screw or other coupling device. Other methods of locking device 100 into position are possible.

FIGS. 1, 2, 6, 7a, 7b, and 8-12 illustrate use of support device 10, 100 with a medical patient chair, for treating a medical patient in the chair, the chair inherently having a projected perimeter when considered in plan view. The embodiments of FIGS. 1, 2, 6, 7a, 7b, and 8 illustrate lateral adjustment of the support device along that portion of the projected perimeter which extends about he back of the medical chair.

The present invention is not limited to use in the dental setting. Such a device can be beneficial in other environments in which individuals expend substantial energy in a forward bent, or forward leaning, position. For example, a lab technician who spends much of the day leaning over a bench can benefit from the present invention. In addition, the present invention can be helpful to others, such as individuals who lean forward over a counter top, desktop or workbench during the course of the day.

Figure 3:
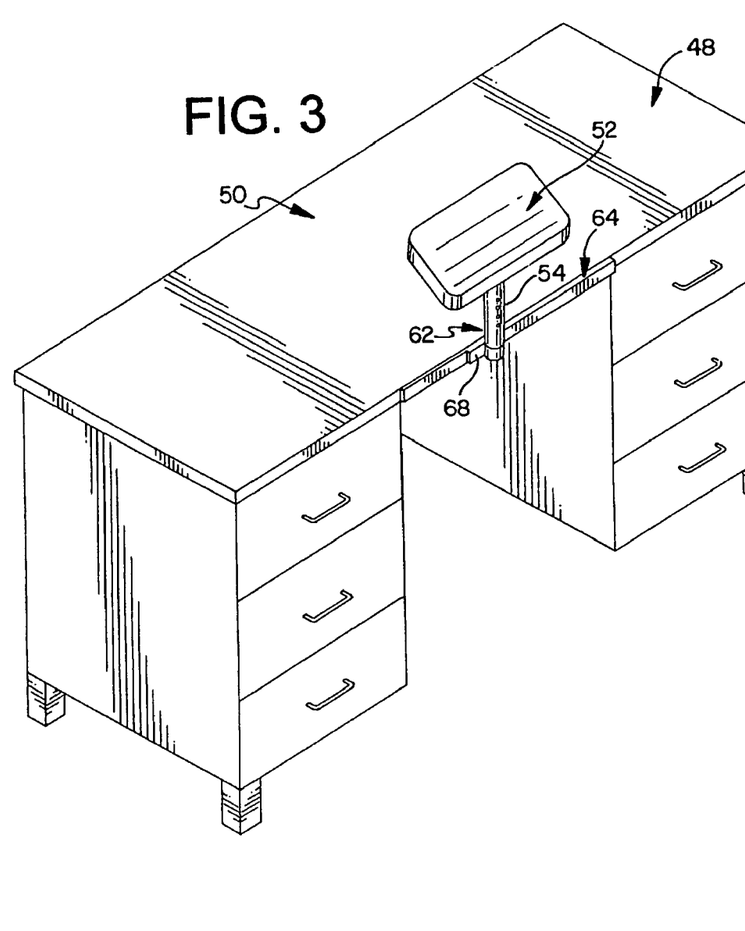
FIG. 3 is a perspective view of an alternate embodiment of the invention in use with a desk.
Figures 4, 5:
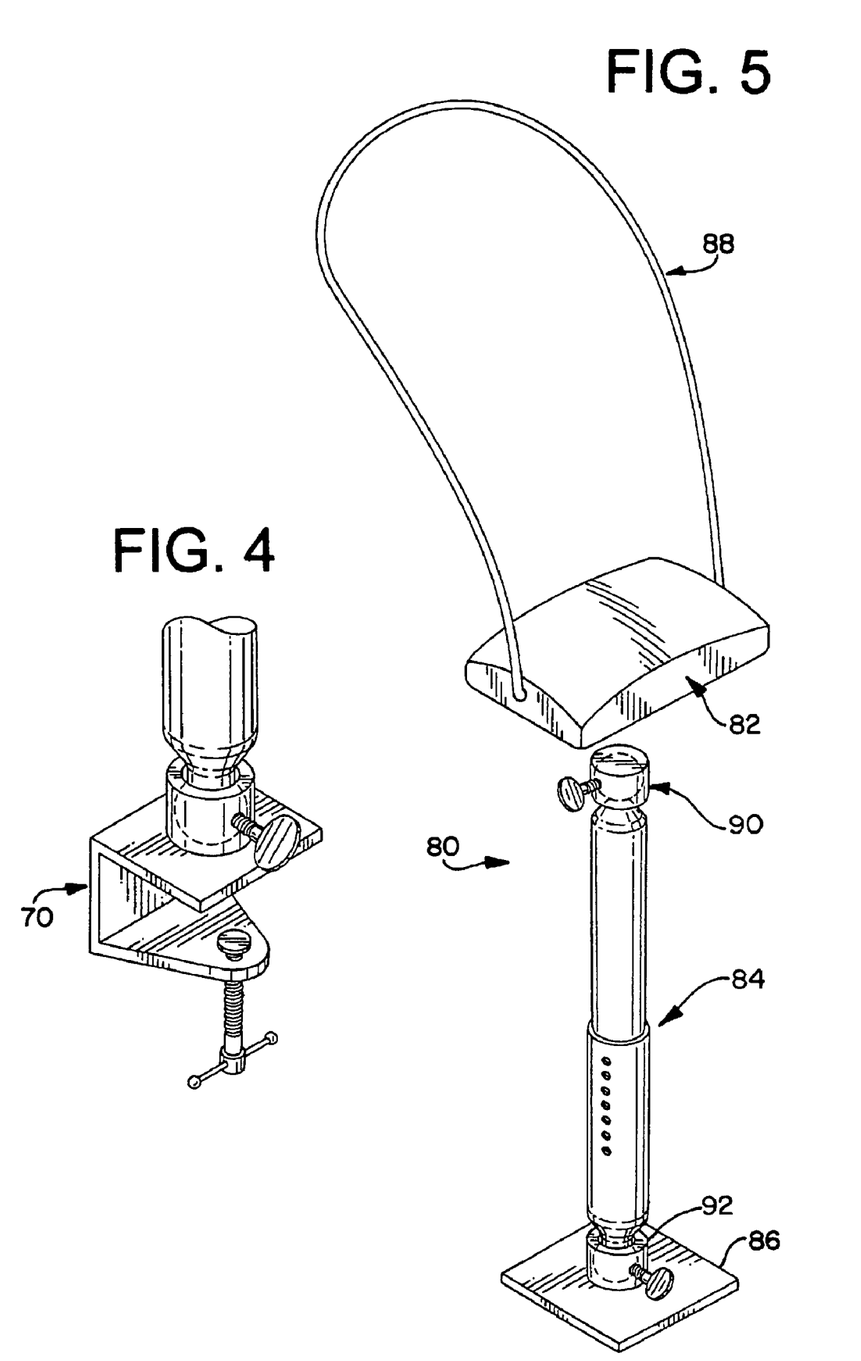
FIG. 4 is a perspective view of an alternate attachment for the embodiment of FIG. 3.
FIG. 5 is a partially exploded, perspective view of another alternate embodiment of the invention for use in activities such as gardening.

For example, FIG. 3 depicts an alternate embodiment 48 of the present invention in use with a desk, table or workbench 50. The embodiment 48 generally comprises a padded rest 52 and an upright bracket 54. To adjust the angle of rest 52, a ball swivel (not shown) with a screw friction lock (not shown), as depicted in FIG. 6, is provided between rest 52 and bracket 54. The bracket 54 is also provided with the telescoping feature of FIGS. 7a and 7b, thereby making the support device, namely rest 52, adjustable in height. To enable the horizontal lateral position of bracket 54 with respect to desk 50 to be adjusted, the lower end of bracket 54 is provided with a slide 62 and desk 50 is provided with a track 64. Slide 62 rides along track 64 in a conventional manner. To lock bracket 54 in a certain position along track 64, a friction lock 68 is engaged. Alternately, the lower end of bracket 54 can be provided with a "C-clamp" type mount 70, as shown in FIG. 4. Such a clamp 70, along with a ball joint pivot, can mount the device directly to the edge of the desk or workbench 50.

The invention is also useful in connection with a variety of recreational, hobby, and other non-vocational activities. Such activities include, but are not limited to, craft work, creation of art works, art restoration, needle work, various activities of senior citizens which are accompanied by a forward lean, reading, and the like. Given the disclosure herein, the support structure necessary to provide anterior support from a base, to the user, can now be readily designed and fabricated by one of ordinary skill in the art for a wide variety of such activities, both vocational, non-vocational, and recreational.

FIG. 5 depicts yet a further embodiment 80 of the present invention for use in recreational activities such as gardening or activities involving kneeling. Such a device can include a padded rest 82, a vertical adjustable bracket 84, and a footplate 86 at the lower end of bracket 84. A neck or shoulder strap 88 can be attached to the support device, as shown at padded rest 82, for carrying the device, thereby allowing the user to change positions without the use of his/her hands.

The device can be provided with a coupling 90 between rest 82 and bracket 84 to vary the angle of rest 82 with respect to bracket 84. In addition, a coupling 92 can also be provided between bracket 84 and footplate 86. Each of these couplings can take the form of a ball swivel with a screw friction lock, similar to that shown in FIG. 6. Bracket 84 can also be provided with the telescoping feature, shown in FIGS. 7a and 7b, to enable the height of bracket 84 to be adjusted.

Figure 13:
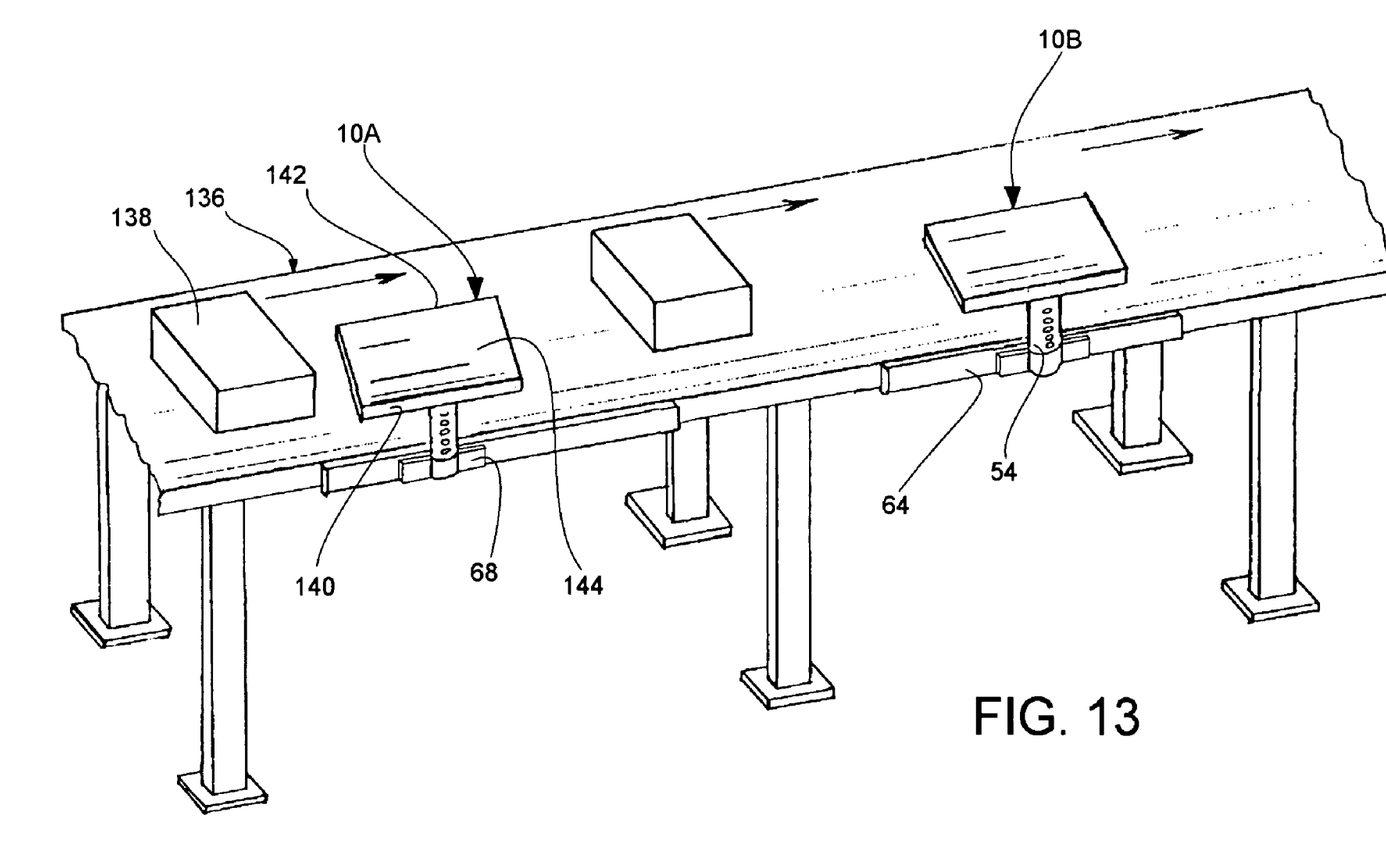
FIG. 13 is a perspective view of use of the invention in a manufacturing line environment.

FIG. 13 illustrates yet another embodiment, wherein support devices 10 of the invention are used in a manufacturing environment. As seen in FIG. 13, first and second support devices 10A, 10B are mounted to a front edge of a manufacturing line 136. Manufacturing line 136, as illustrated, comprises an elongate work space, or base, for example a structural support frame, having a top surface such as a table top, or a conveyor belt, on which work pieces 138 are disposed. Structures other than flat surfaces can be used to support work pieces. For example, pins, hooks, chains, frames, as well as a wide variety of other known structures can be used as support structure to support work pieces.

Support devices 10 are mounted at the front edge of the work space, at spaced locations along the length of the manufacturing line. Each support device 10 includes a rest 12, supported on a support bracket 54, from a friction lock 68 which is supported by track 64 and which, when unlocked, can slide along track 64.

As in the embodiment of e.g. FIG. 3, bracket 54 can be adjusted for height if and as desired, using e.g. similar hole and pin adjustment structures.

Rest 12 can pivot on pivot structure (not shown) between bracket 54 and rest 12. Such pivotation generally pivots the rest about an axis which is generally aligned with the length of manufacturing line 136.

Rest 12 has a front 140, a rear 142, and an interfacing top surface 144. The pivotation of support device 10 enables a worker to approach support device 10 from the front, lean the front side of his/her torso on the interfacing top surface of rest 12, and adjust the angle of the rest with respect to a horizontal plane, to generally match the angle of inclination of the front of his/her torso, such that rest 12 is generally aligned with the front of the torso, thereby achieving maximum surface-to-surface contact between the surface of the torso and the interfacing top surface of the rest, thereby achieving a very comfortable distribution of the weight of the torso on the rest.

In some instances, rest 12 is then allowed to pivot dynamically in real time, thus to continuously adjust the angle of the rest to the movements of the worker's body as the worker applies weight on the rest. In other instances, the rest is then locked in a fixed pivot orientation once a desired orientation is achieved.

In either case, the worker leans forward, resting his/her upper body weight on the rest e.g. while working on work pieces 138 on the manufacturing line.

As referred to herein, including in the claims which follow, the "base" can be any foundation from which the rest is supported. The base can be below the rest, above the rest, and at any orientation, including horizontal, vertical, or any angle between horizontal and vertical. The base can have a wide variety of configurations so long as the base provides a foundation from which the rest is supported. Accordingly, the base can be, for example, the floor itself, a floor-mounted bracket, a ceiling-mounted bracket, a wall-mounted bracket, a bracket mounted on a structure which is mounted to the floor, the ceiling, or a wall. The base can be a substantially massive object which is stabilized from e.g. the floor, ceiling, or wall. An example of such base is heavy chair such as a dental chair, a frame which supports a work station, or the like.

As used herein, including in the claims which follow, the terms "manufacture", "manufacturing", and the like refer to a wide variety of man-made transformations of matter, including physical, chemical, electrical, or other transformations or materials, including but not limited to, assembly of multiple parts, or combining of parts. "Manufacture", and "manufacturing" include such activities as modifying work pieces, assembling multiple piece parts and/or subassemblies into assemblies of next-level subassemblies, and operations which include both work piece modification and assembling piece parts and/or subassemblies together.

While the invention has been described in connection with certain embodiments, it should be understood that it is not intended to limit the invention to these particular embodiments. To the contrary, it is intended to cover all alternatives, modifications and equivalents falling within the spirit and scope of the invention.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A support device adapted and configured to support a user's torso, said support device adapted to be used with a patient chair, said patient chair having a base, said support device comprising:

a) a padded rest which a user, who is not a patient seated in said patient chair, can lean his torso against, said torso includes said user's abdominal area, chest area and anterior shoulder area;

b) a transport structure including a horizontal track which is connected to said base, said transport structure capable of moving linearly along said base on said horizontal track, said transport structure capable of being temporarily fixed in a first position along said horizontal track against linear movement with respect to said base, and said transport structure capable of being subsequently released from said first position so as to again enable linear movement of said transport structure along said base on said horizontal track; and c) a support structure connecting said transport structure to said padded rest, said support structure having an angled bracket secured to said padded rest which permits said padded rest to pivot with respect to said angled bracket, an upright bracket secured to said transport structure, and a coupler joining said angled bracket to said upright bracket, said coupler allowing said angled bracket to be tilted relative to said upright bracket in any direction, and said coupler including a ball swivel having a screw friction lock.

2. The support device of claim 1 wherein said transport structure is adapted and configured to be operatively coupled to one of the group consisting of: a dental chair, said base located adjacent to a dental chair, and a desk.

3. The support device of claim 2 wherein said coupler permits said padded rest to pivot relative to said transport structure.

4. The support device of claim 3 wherein said pivot structure enables said padded rest to pivot with respect to said angled bracket.

5. The support device of claim 1 wherein said coupler permits said padded rest to pivot relative to said support structure.

6. The support device of claim 5 wherein said pivot structure enables said padded rest to pivot with respect to said angled bracket.

7. The support device of claim 6 further comprising an extension structure operative with at least one of said transport structure, said support structure, and said padded rest, so as to enable said padded rest to be extended further away from, and/or retracted toward, said base.

8. The support device of claim 1 further comprising an extension structure operative with at least one of said transport structure, said support structure, and said padded rest, so as to enable said padded rest to be extended further away from, and/or retracted toward, said base.

9. The support device of claim 1 wherein said transport structure comprises a track, having a length, and said support structure being operatively movable along said length of said track.

10. A support device adapted and configured to support a user's torso, said support device adapted to be used with a patient chair, said patient chair having a base, said support device comprising:
   a) a padded rest which a user, who is not a patient seated in said patient chair, can lean his torso against, said padded rest having a front and a rear, said padded rest being adapted, configured and mounted such that a user can approach said padded rest from said front and lean his torso on said padded rest, and said torso includes said user's abdominal area, chest area and anterior shoulder area;
   b) a transport structure including a horizontal track which is connected to said base, said transport structure capable of moving linearly along said base on a said horizontal track, said transport structure capable of being temporarily fixed on said horizontal track in a first position against linear movement with respect to said base, and said transport structure capable of being subsequently released from said first position so as to again enable linear movement of said transport structure along said base on said horizontal track; and
   c) a support structure connecting said transport structure to said padded rest, said support structure having an angled bracket secured directly to said padded rest which permits said padded rest to pivot with respect to said angled bracket, an upright bracket secured to said transport structure, and a coupler joining said angled bracket to said upright bracket, said coupler allowing said angled bracket to be tilted relative to said upright bracket in any direction.

11. The support device of claim 10 wherein said padded rest pivots with respect to said support structure, about a pivot axis which extends in a direction parallel to at least a portion of said track traversed by said transport structure.

12. The support device of claim 11 further comprising an extension structure operative with at least one of said transport structure, said support structure, and said padded rest, so as to enable said padded rest to be extended further away from, and/or retracted toward, said base.

13. The support device of claim 10 wherein said transport structure is adapted and configured to be operatively coupled to one of the group consisting of: a dental chair, said base located adjacent to a dental chair, and a desk.

14. The support device of claim 10 further comprising an extension structure operative with at least one of said transport structure, said support structure, and said padded rest, so as to enable said padded rest to be extended further away from, and/or retracted toward, said base.

15. A support device adapted and configured to support a user's torso, said support device adapted to be used with a patient chair, said patient chair having a base, said support device comprising:
   a) a padded rest which a user, who is not a patient seated in said patient chair, can lean his torso against, and said torso includes said user's abdominal area, chest area and anterior shoulder area;
   b) a transport structure including a horizontal track which is connected to said base, said transport structure capable of moving linearly along said base on said horizontal track, said transport structure capable of being temporarily fixed in a first position along said horizontal track against linear movement with respect to said base, and said transport structure capable of being subsequently released from said first position so as to again enable linear movement of said transport structure along said base on said horizontal track; and
   c) a support structure connecting said transport structure to said padded rest, said support structure having an angled bracket pivotably coupled by a pivot structure to said padded rest, an upright bracket secured to said transport structure, and a coupler joining said angled bracket to said upright bracket, said coupler allowing said angled bracket to be tilted relative to said upright bracket in any direction, and said coupler including a ball swivel having a screw friction lock.

16. The support device of claim 15 wherein said padded rest has a front and a rear, said padded rest being adapted and configured such that a user can approach said padded rest from said front and lean his torso on said padded rest, and across an axis of pivotation of said pivot structure.

17. The support device of claim 16 wherein said pivot structure enables said padded rest to pivot with respect to said support structure.

18. The support device of claim 15 wherein said transport structure is adapted and configured to be operatively coupled to one of the group consisting of: a dental chair, said base located adjacent to a dental chair, and a desk.

19. The support device of claim 18 further comprising an extension structure operative with at least one of said transport structure, said support structure, and said padded rest, so as to enable said padded rest to be extended further away from, and/or retracted toward, said base.

20. The support device of claim 15 wherein said pivot structure enables said padded rest to pivot with respect to said support structure.

21. The support device of claim 15 further comprising an extension structure operative with at least one of said transport structure, said support structure, and said padded rest, so as to enable said padded rest to be extended further away from, and/or retracted toward, said base.

22. The support device of claim 15 further comprising an extension structure operative with at least one of said transport structure, said support structure, and said padded rest, said extension structure enabling said padded rest to be extended further away from, and/or retracted toward said base.

23. The support device of claim 15 wherein said horizontal track has a length, and said support structure is operatively movable along said length.

24. The support device of claim 23 wherein at least one of said horizontal track and said support structure comprises a locking structure adapted and configured to temporarily lock said support structure against movement along said length of said horizontal track.

25. A support device adapted and configured to support a user's torso, said support device adapted to be used with a work station, said support device comprising:
   a) a substrate effective to support an object on which work is to be performed;
   b) a padded rest which a user can lean his torso against while working on said object in association with said substrate, said torso includes said user's abdominal area, chest area and anterior shoulder area;
   c) a transport structure including a horizontal track which is connected to said substrate, said transport structure capable of moving linearly along said substrate on said horizontal track, said transport structure capable of being temporarily fixed in a first position along said horizontal track against linear movement with respect to said substrate, and said transport structure capable of being subsequently released from said first position so as to again enable linear movement of said transport structure along said substrate on said horizontal track; and
   d) a support structure connecting said transport structure to said padded rest, said support structure having an angled bracket secured to said padded rest which permits said padded rest to pivot with respect to said angled bracket, an upright bracket secured to said transport structure, and a coupler joining said angled bracket to said upright bracket, said coupler allowing said angled bracket to be tilted relative to said upright bracket in any direction, and said coupler including a ball swivel having a screw friction lock.

26. The support device of claim 25 further comprising a pivot structure operatively engaged in at least one of said padded rest and said support structure.

27. The support device of claim 25 wherein said transport structure is adapted and configured to be operatively coupled to a desk.

28. The support device of claim 25 further comprising an extension structure operative with at least one of said transport structure, said support structure, and said padded rest, said extension structure enabling said padded rest to be extended further away from, and/or retracted toward said substrate.

29. A support device adapted and configured to support a user's torso, said support device adapted to be used with a manufacturing facility having work stations where manufacturing work is to be performed by workers as the predominant work at said work stations, each of said work stations including a support device, said support device comprising:
   a) a padded rest which a user can lean his torso against, said torso includes said user's abdominal area, chest area and anterior shoulder area;
   b) a transport structure including a horizontal track which is connected to each of said work stations, said transport structure capable of moving linearly along said horizontal track, said transport structure capable of being temporarily fixed in a first position along said horizontal track against linear movement with respect to said respective work station, and said transport structure capable of being subsequently released from said first position so as to again enable linear movement of said transport structure along said respective work station on said horizontal track; and
   c) a support structure connecting said transport structure to said padded rest, said support structure having an angled bracket secured to said padded rest which permits said padded rest to pivot with respect to said angled bracket, an upright bracket secured to said transport structure, and a coupler joining said angled bracket to said upright bracket, said coupler allowing said angled bracket to be tilted relative to said upright bracket in any direction, and said coupler including a ball swivel having a screw friction lock.

30. The support device of claim 29 wherein said transport structure is coupled to each of said work stations, and said transport structure serves as an interface between said work station and said support structure, the coupling of said transport structure to said work station being operative to enable movement of said transport structure, and thus said support device, with respect to said work station.

31. The support device of claim 30 further comprising a pivot structure operatively engaged in at least one of said padded rest and said support structure.

32. The support device of claim 31 wherein said at least first and second work stations are disposed inside a generally closed building.

33. The support device of claim 29 further comprising a pivot structure operatively engaged in at least one of said padded rest and said support structure.

34. The support device of claim 33 wherein said pivot structure enables said padded rest to pivot with respect to said support structure.

35. The support device of claim 29 wherein said at least first and second work stations are disposed inside a generally closed building.

36. The support device of claim 29 wherein said padded rest comprises an interfacing surface sufficiently expansive in length and width that a user thereof can comfortably lean the weight of his torso on said interfacing surface, and wherein said support device includes an adjustment structure which enables adjustment of said padded rest with respect to said work station, regarding at least one of height of said padded rest, and angle of said interfacing surface with respect to a horizontal plane.

37. The support device of claim 36 wherein said adjustment structure enables said padded rest to pivot with respect to said support structure.

38. The support device of claim 29 wherein said horizontal track has a length, and said support structure is operatively movable along said length.

39. The support device of claim 38 further comprising a locking structure adapted and configured to temporarily lock said support structure against movement along said length of said horizontal track.

* * * * *